US006527767B2

(12) United States Patent
Wang et al.

(10) Patent No.: US 6,527,767 B2
(45) Date of Patent: *Mar. 4, 2003

(54) CARDIAC ABLATION SYSTEM AND METHOD FOR TREATMENT OF CARDIAC ARRHYTHMIAS AND TRANSMYOCARDIAL REVASCULARIZATION

(75) Inventors: Paul J. Wang, Chestnut Hill; Hassan Rastegar, Newton, both of MA (US)

(73) Assignee: New England Medical Center, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/082,047

(22) Filed: May 20, 1998

(65) Prior Publication Data

US 2002/0058934 A1 May 16, 2002

(51) Int. Cl.⁷ ............................................... A61B 18/04
(52) U.S. Cl. ............................ 606/32; 606/41; 607/99; 128/898
(58) Field of Search .................. 606/32, 41, 45, 606/46, 47, 48, 49, 50; 607/129, 130, 99; 128/898

(56) References Cited

U.S. PATENT DOCUMENTS

| 5,156,151 A | 10/1992 | Imran ........................ 128/642 |
| 5,396,887 A | 3/1995 | Imran ........................ 128/642 |
| 5,400,783 A | 3/1995 | Pomeranz et al. .......... 128/642 |
| 5,427,119 A | 6/1995 | Swartz et al. ............. 128/772 |
| 5,443,463 A | 8/1995 | Stern et al. ................. 606/51 |
| 5,452,733 A | 9/1995 | Sterman et al. ............ 128/898 |
| 5,462,545 A | 10/1995 | Wang et al. ................. 606/41 |

(List continued on next page.)

FOREIGN PATENT DOCUMENTS

| WO | WO 95/10318 | 4/1995 |
| WO | WO 95/10319 | 4/1995 |
| WO | WO 95/10320 | 4/1995 |
| WO | WO 95/10321 | 4/1995 |
| WO | WO 95/10978 | 4/1995 |
| WO | 96/26675 | 1/1996 |
| WO | WO 96/10961 | 4/1996 |
| WO | WO 96/39966 | 12/1996 |

(List continued on next page.)

OTHER PUBLICATIONS

Avitall et al., "A Thoracoscopic Approach to Ablate Atrial Fibrillation Via Linear radiofrequency Lesion Generation on the Epicardium of Both Atria", (1996) Pace 19: 626.

(List continued on next page.)

Primary Examiner—Rosiland S. Kearney
(74) Attorney, Agent, or Firm—Hoekendijk & Lynch, LLP

(57) ABSTRACT

A medical device, and related method, use epicardial ablators and detectors for intraoperative epicardial approaches to ablation therapy of cardiac conduction pathways. An epicardial gripper is sized to grasp the cardiac circumference or smaller structures on the epicardial surface of the heart. Ablators are disposed on the arms of the gripper for epicardial ablation of cardiac conduction tissue. In another embodiment of the invention, an electrode system includes a flexible, adjustable probe forming a loop for epicardial ablation. Ablators are provided on one or multiple surfaces of the probe for epicardial ablation of cardiac conduction tissue. In yet another embodiment of the invention, an endocardial ablator detection system provides an indicator adjacent an ablator on an endocardial catheter, and a detector on an epicardial probe. The epicardial probe detects signals transmitted by the indicator on the endocardial catheter to localize the position of the endocardial ablator relative to the epicardial surface. The surgeon uses this information for guidance in adjusting the position of the endocardial ablator according to therapeutic objectives of cardiac ablation.

16 Claims, 13 Drawing Sheets

U.S. PATENT DOCUMENTS

| | | | |
|---|---|---|---|
| 5,497,774 A | 3/1996 | Swartz et al. | 128/658 |
| 5,505,730 A | 4/1996 | Edwards | 606/41 |
| 5,555,883 A | 9/1996 | Avitall | 128/642 |
| 5,558,073 A | 9/1996 | Pomeranz et al. | 128/642 |
| 5,571,215 A | 11/1996 | Sterman et al. | 623/66 |
| 5,575,766 A | 11/1996 | Swartz et al. | 604/53 |
| 5,575,788 A | 11/1996 | Baker et al. | 606/41 |
| 5,575,810 A | 11/1996 | Swanson et al. | 607/99 |
| 5,595,183 A | 1/1997 | Swanson et al. | 128/697 |
| 5,617,854 A | 4/1997 | Munsif | 128/642 |
| 5,637,090 A | 6/1997 | McGee et al. | 604/95 |
| 5,673,695 A | 10/1997 | McGee et al. | 128/642 |
| 5,676,662 A | 10/1997 | Fleischhacker et al. | 606/41 |
| 5,687,723 A | 11/1997 | Avitall | 128/642 |
| 5,688,267 A | 11/1997 | Panescu et al. | 606/41 |
| 5,690,611 A | 11/1997 | Swartz et al. | 604/53 |
| 5,730,127 A | 3/1998 | Avitall | 128/642 |
| 5,730,704 A | 3/1998 | Avitall | 600/374 |
| 5,733,280 A | 3/1998 | Avitall | 606/23 |
| 5,797,960 A | 8/1998 | Stevens et al. | 606/213 |
| 5,904,711 A * | 5/1999 | Flom et al. | 607/129 |
| 6,142,994 A * | 11/2000 | Swanson et al. | 606/41 |
| 6,152,920 A * | 11/2000 | Thompson et al. | 606/41 |
| 6,161,543 A | 12/2000 | Cox et al. | 128/898 |
| 6,237,605 B1 * | 5/2001 | Vaska et al. | 128/898 |
| 6,245,064 B1 * | 6/2001 | Lesh et al. | 606/34 |

FOREIGN PATENT DOCUMENTS

| | | |
|---|---|---|
| WO | WO 97/06727 | 2/1997 |
| WO | WO 97/17904 | 5/1997 |
| WO | WO 97/25916 | 7/1997 |
| WO | WO 97/25918 | 7/1997 |
| WO | WO 97/25919 | 7/1997 |
| WO | WO 97/32525 | 9/1997 |
| WO | WO 97/37607 | 10/1997 |
| WO | WO 97/45156 | 12/1997 |

OTHER PUBLICATIONS

Chevalier et al., "Video–assisted Thoracoscopic Radio Frequency Catheter Ablation of the Left Atrium Prevents Inducibility of Atrial Fibrillation in Dogs", Circulation (1997) 96: 575.

Cox, J.L. et al., "The Surgical Treatment of Atrial Fibrillation. III. Development of a Definitive Surgical Treatment", J. thorac Cardiovasc Surg. (1991) 101: 569–583.

Jais, P. et al., "Catheter Ablation for Paroxysmal Atrial Fibrillation: High Success Rates with Ablation in the Left Atrium", Circulation (1996) 94: I–675.

Lindsay et al., "Intraoperative Observation and Epicardial Mapping after Attempted Catheter Ablation of Atrial Fibrillation", Circulation (1997) 96:450.

Nakagawa et al., "Use of Atrial Potential Attenuation to Identify Endpoint of Radiofrequency Application for Continuous Transmural Linear Atrial Ablation", Circulation (1997) 96: 577.

Lee et al., "Minimally Invasive Epicardial Atrial Linear Ablation Using Cooled Radiofrequency Energy", Circulation (1997) 96: 577.

Sharma et al., "A Comparison of Sequential with Simultaneous Delivery of RF Energy Application at Multiple Electrodes to Produce Linear Continuous Lesions", Circulation (1997) 96: 576.

Sie, H.T. et al., "Radiofrequency Ablation of Atrial Fibrillation in Patients Undergoing Mitral Valve Surgery: First Experience", Circulation (1996) 84: I–675.

Sie et al., "Radiofrequency Ablation of Atrial Fibrillation in Patients Undergoing Valve Surgery", Ciculation (1997) 96: 450.

Thomas et al., "An Endocardial Radiofrequency Ablative Technique for Cure of Atrial Fibrillation During Cardiac Surgery", Circulation (1997) 96: 450.

* cited by examiner

LEFT SIDE OF HEART: SAGITTAL SECTION

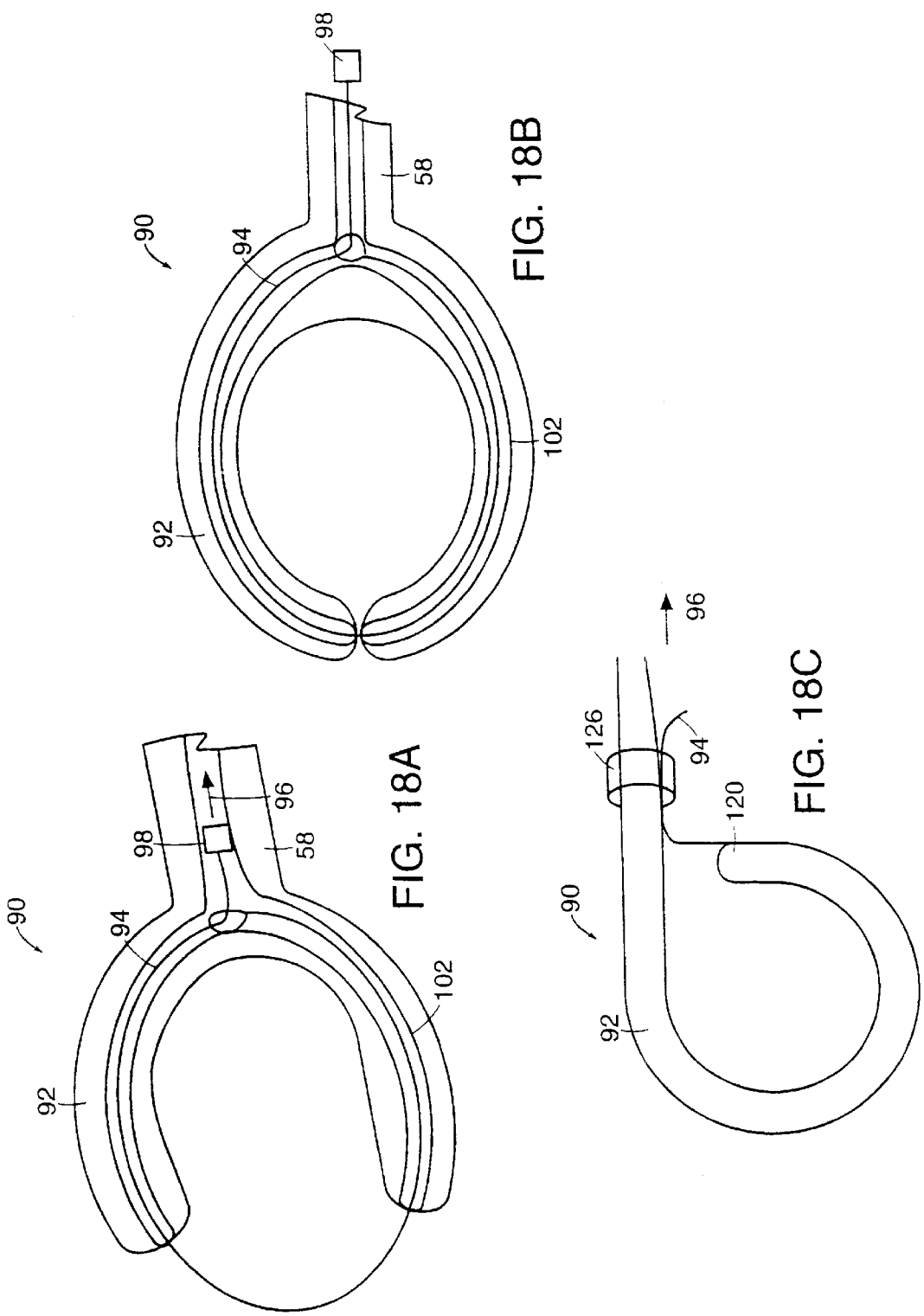

CARDIAC ABLATION SYSTEM AND METHOD FOR TREATMENT OF CARDIAC ARRHYTHMIAS AND TRANSMYOCARDIAL REVASCULARIZATION

BACKGROUND OF THE INVENTION

Tachycardia is a type of cardiac arrhythmia and is a serious, often-times, fatal condition characterized by rapid, uncontrolled, and ineffective beating of the heart. Most tachycardia is one of two broad categories: ventricular tachycardia (hereinafter VT) and supraventricular tachycardia (hereinafter SVT). VT occurs in the lower chambers of the heart, the ventricles, and frequently leads to serious complications, including sudden cardiac death. Atrial fibrillation and flutter, forms of SVT, originate in the upper chambers of the heart, the atria, and often result in chest pain, fatigue and dizziness and, while generally not life-threatening, is a leading cause of stroke in the United States.

Currently, many cases of VT and SVT are treated by drugs that modify the electrical characteristics of the heart tissue. However, the drugs do not eliminate or may not completely control the arrhythmia. In many cases of sustained VT, implantable cardiac defibrillators are used which deliver powerful shocks to the heart when fibrillation is detected. Concurrent treatment with drugs is standard therapy and each implantation of a cardiac defibrillator, of which there may be more than one per patient, is very expensive.

Some forms of SVT are treated by endocardial ablation, a minimally invasive procedure. During endocardial ablation, a mapping catheter is passed through an artery or vein into the patient's heart to find the site(s) of the arrhythmogenic tissue, the tissue from which the tachycardia originate. This same catheter or a separate catheter is used to transmit sufficient energy to thermally damage the tissue either by heating or cooling. (FIG. 1)

In atrial fibrillation the regular pumping action of the atria is replaced by a disorganized, ineffective quivering caused by chaotic conduction of electrical signals through the upper chambers of the heart. Although not immediately life threatening, atrial fibrillation may cause up to a 30% reduction in cardiac output and can lead to more serious conditions, including the formation of blood clots in the atria that can dislodge and travel to the brain resulting in stroke. Currently, the only curative treatment for atrial fibrillation is the surgical "maze procedure", an open heart procedure in which the surgeon makes several incisions in the right and left atria creating scar tissue to electrically separate portions of the atria. Despite clinical success of the maze procedure, it is time-consuming and demanding. The procedure requires open heart surgery and is very expensive. Accordingly, only a modest number of maze procedures are performed annually in a limited number of centers.

Another use of ablation technology, either endocardial or epicardial, is transmyocardial revascularization. The creation of small ablation holes results in genesis of new blood vessels, providing a source of blood flow in areas of the heart not receiving sufficient blood.

The present invention provides another apparatus and method for treating cardiac arrhythmia, that may be widely applicable. The present invention also provides an apparatus for transmyocardial revascularization.

SUMMARY OF THE INVENTION

The present invention provides devices and methods for epicardial and endocardial approaches for myocardial ablation for treatment of cardiac arrhythmias and myocardial revascularization.

One aspect of the invention provides a gripper for grasping the epicardial surface of the heart for the purpose of ablating cardiac tissue. In one embodiment, the arms of the gripper are sized and dimensioned to substantially encircle the circumference of the heart or a portion of it, thereby stabilizing the gripper against the contracting heart. The ablators are sized and positioned on one or more of the arms of the gripper according to the location and geometry of the cardiac tissue to be ablated.

In another embodiment, the gripper is sized and dimensioned to encompass structures on the surface of the heart. In yet another embodiment of this aspect of the invention, one arm of the gripper is inserted through an incision in the wall of the heart into one of the heart chambers. The other arm or arms of the gripper are positioned on the epicardial surface to stabilize the heart. The ablators are located on an arm or arms in an array according to the location and geometry of the tissue to be ablated. In one embodiment, the gripper ablates both the epicardial and endocardial surfaces.

In one embodiment, one or more of the arms may form an array. One embodiment of the array is a Y. Another embodiment of the array are loops or spokes.

Another aspect of the invention is an electrode system comprising a probe in the form of an adjustable, flexible substrate forming a substantially closed loop for epicardial ablation. In one embodiment of the invention, the loop is sized to substantially encompass a structure on the epicardial surface of the heart. In another embodiment, the loop is substantially sized to encircle the circumference of the heart. The cross section of the probe may be round, oval, multi-faceted or have multiple radii. In one embodiment the probe does not encompass the entire circumference of a portion of the heart.

In another embodiment of this aspect of the invention, the size of the substantially closed loop comprising the probe is adjustable by a pull string attached to one end of the probe. In another embodiment the probe substrate comprises an elastomeric material. The loop of the elastomeric probe is adjustable by expanding or contracting the probe.

In another embodiment of this aspect of the invention, the electrode system is sized and dimensioned for insertion through an endoscope or thoracoscope. In yet another embodiment, the electrode system includes attachments such as, for example, a cooling system in communication with the probe or a gripping device such as a suction device in communication with the probe.

In one particular embodiment of the invention, the electrode system comprises a glove and an ablator in communication with one or more fingers of the glove.

The ablators of the electrode system are positioned generally to correspond to the cardiac tissue to be ablated. In one embodiment, the ablators are positioned on the inner surface of the probe. In another embodiment, the ablators are positioned on more than one surface of the probe. For example, the ablators may be positioned on the flat surface of a probe with a D-shaped cross section, on one semi-circle of a circular cross section, or on one or more surfaces of a rectangular cross section. The ablators may be located on one or more arms in any configuration.

In a preferred embodiment of this aspect of the invention, the ablators may be individually and independently activated. In another particular embodiment, the ablators are removably attached to the probe substrate.

Another aspect of this invention comprises an endocardial ablator-detection and ablation system for performing transmyocardial ablation. The ablator-detection and transmyocardial ablation system provides an indicator located on an endocardial ablating catheter adjacent an ablator, and a detector located on an epicardial probe. The indicator located on the endocardial ablating catheter transmits a signal indicating the position of the ablator on the catheter. The epicardial detector receives the signal thereby localizing the relative epicardial position of the ablator on the endocardial catheter. Ablating energy is applied when the ablator is appropriately positioned.

In one embodiment of the endocardial ablator detection system, the indicator is a magnet and the detector is a magnetic field detector. In another embodiment of the detection system, the indicator is a light transmitter, such as, for example, laser light, and the epicardial detector comprises a light detector. In another embodiment of the system the indicator is a light source emitting fluorescent light and the epicardial detector detects light in the wavelength of fluorescence. In yet another embodiment of the invention, the epicardial detector comprises an ultrasound detector, or an echocardiograph. In yet another embodiment, a magnet in the epicardial probe attracts a magnetic or metallic element in the endocardial ablator, guiding the ablators into position.

In any aspect of the invention, cooling or ablating energy may be applied by the ablators to ablate cardiac tissue. In one embodiment, cooling fluid travels via a lumen in the ablator and exits via small holes carrying the fluid through another lumen that exits from the catheter. The change in pressure or phase change results in cooling or freezing. The ablating energy applied to ablate cardiac tissue in any aspect of the invention may be thermal, radio frequency, direct current, ultrasound or laser energy.

BRIEF DESCRIPTION OF THE DRAWINGS

FIG. 18A is a diagrammatic view of the pull-string adjustable flexible probe of the electrode system in open position;

FIG. 18B is a diagrammatic view of the pull-string flexible probe of the electrode system in closed position;

FIG. 18C is another embodiment of the pull-string flexible probe;

DESCRIPTION

Anatomy of the Heart

Figure 1:
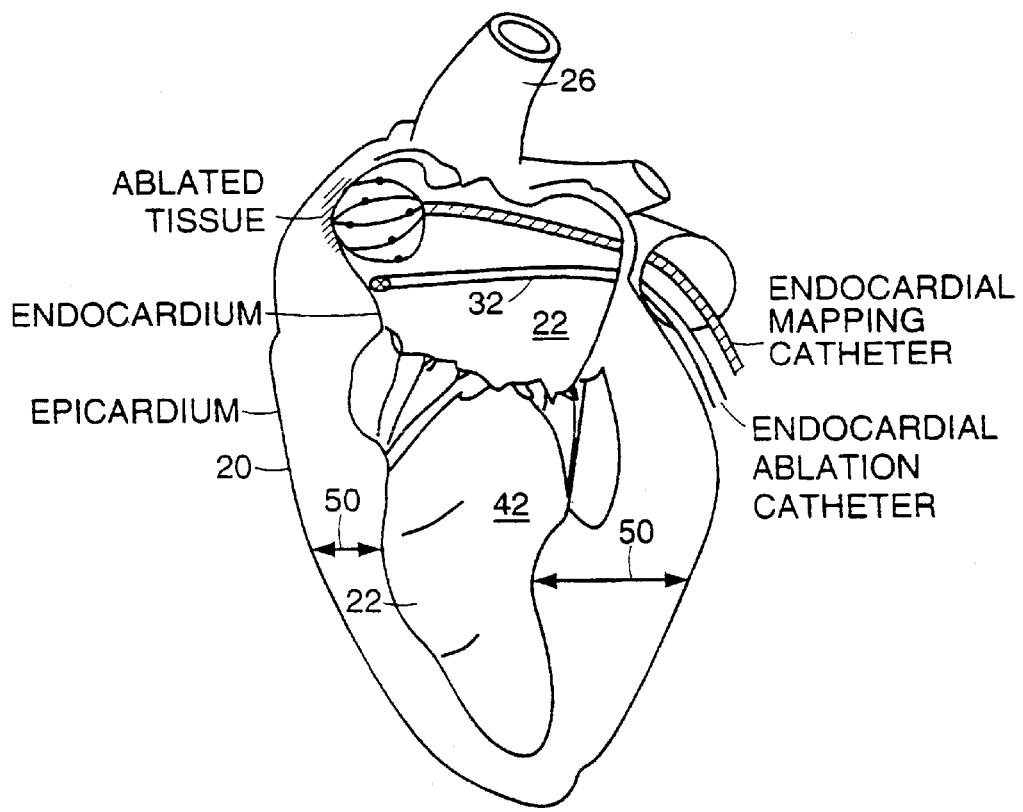
FIG. 1 is a simplified and diagrammatic sagittal section view of the interior of the left side of the heart showing an endocardial ablating catheter of the prior art within a large vessel and left atrium.
Figure 2A:
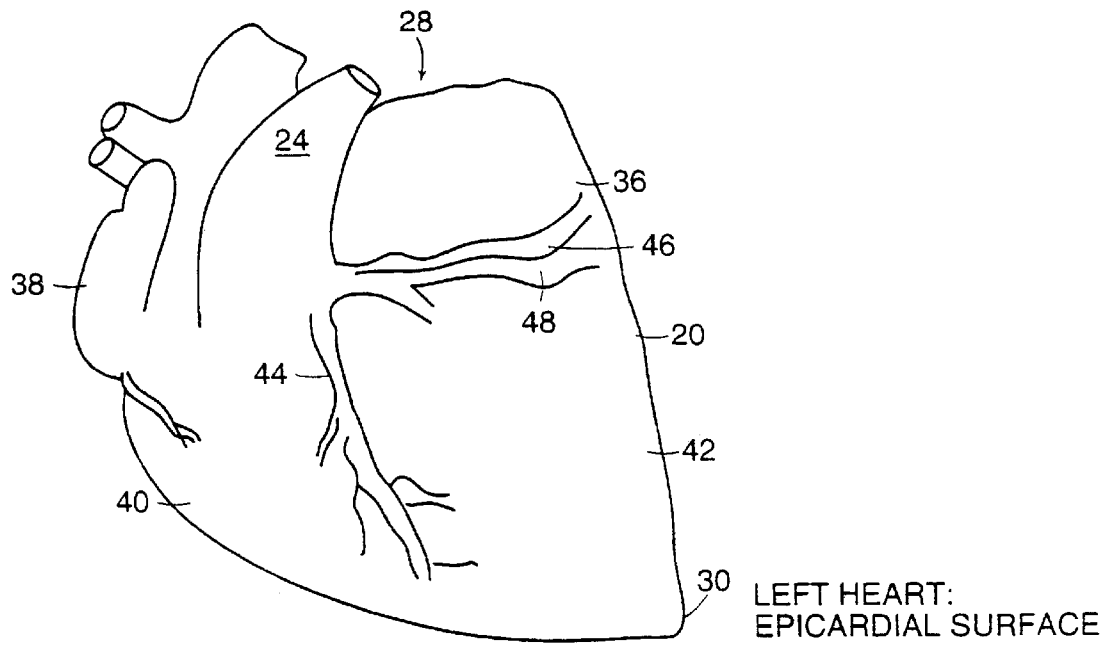
FIG. 2A is a simplified and diagrammatic view of the anterior surface of the left heart and FIG. 2B is a simplified and diagrammatic view of the posterior surface of the right heart.
Figure 2B:
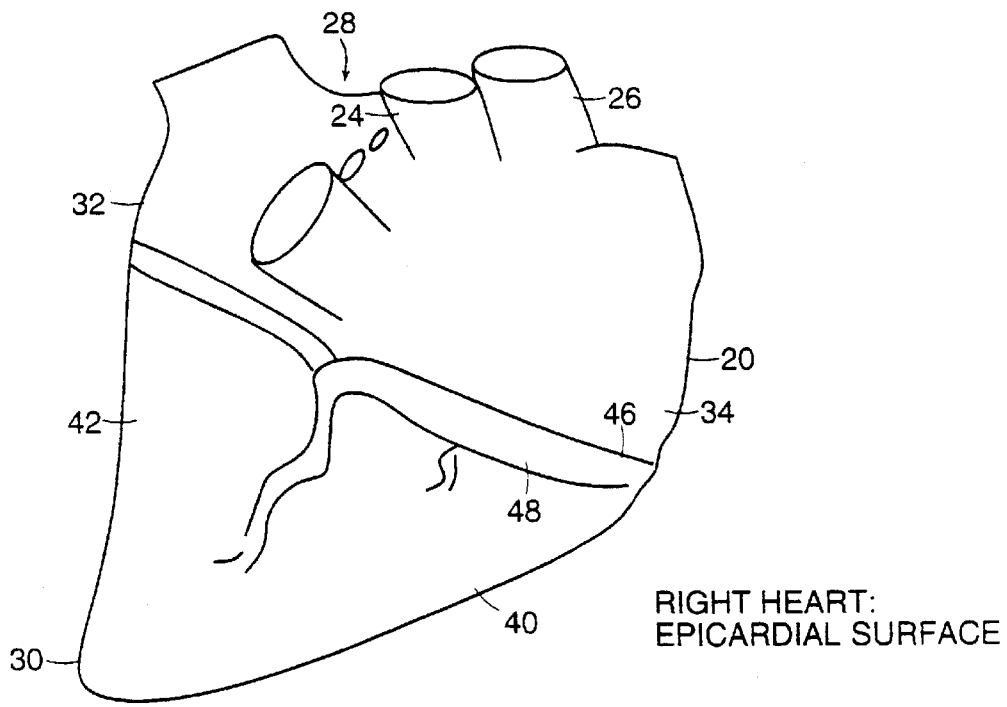

The heart as shown in FIG. 1 has at least two surfaces, an outer surface, the epicardium 20, and an inner surface, the endocardium 22. Numerous cardiac structures are identifiable on the epicardial surface 20. For example, as illustrated in FIGS. 2A and B, the pulmonary artery 24 and aorta 26 exit from the epicardial surface 20 at the base 28 of the heart. The apex 30 of the heart is the pointed end of the heart opposite the base 28 of the heart. The left atrium 32 and right atrium 34 are readily identifiable by the left 36 and right 38 auricles. The right ventricle 40 and left ventricle 42 are localized by identifying the left longitudinal groove 44 which runs from approximately the heart base 28 to apex 30 on the epicardial surface 20. The coronary groove 46 on the epicardial surface 20 separates the cardiac atria 32, 34 from the cardiac ventricles 42, 40. The great coronary vessels 48 are disposed in the coronary groove 46.

The endocardium 22 lines the inside walls of both types of heart chambers, i.e., the atria and the ventricles as illustrated in FIG. 1. The endocardial surface 22 opposes the epicardial surface 20 and is separated by the thick muscular wall of the heart, the myocardium 50.

Figure 3:
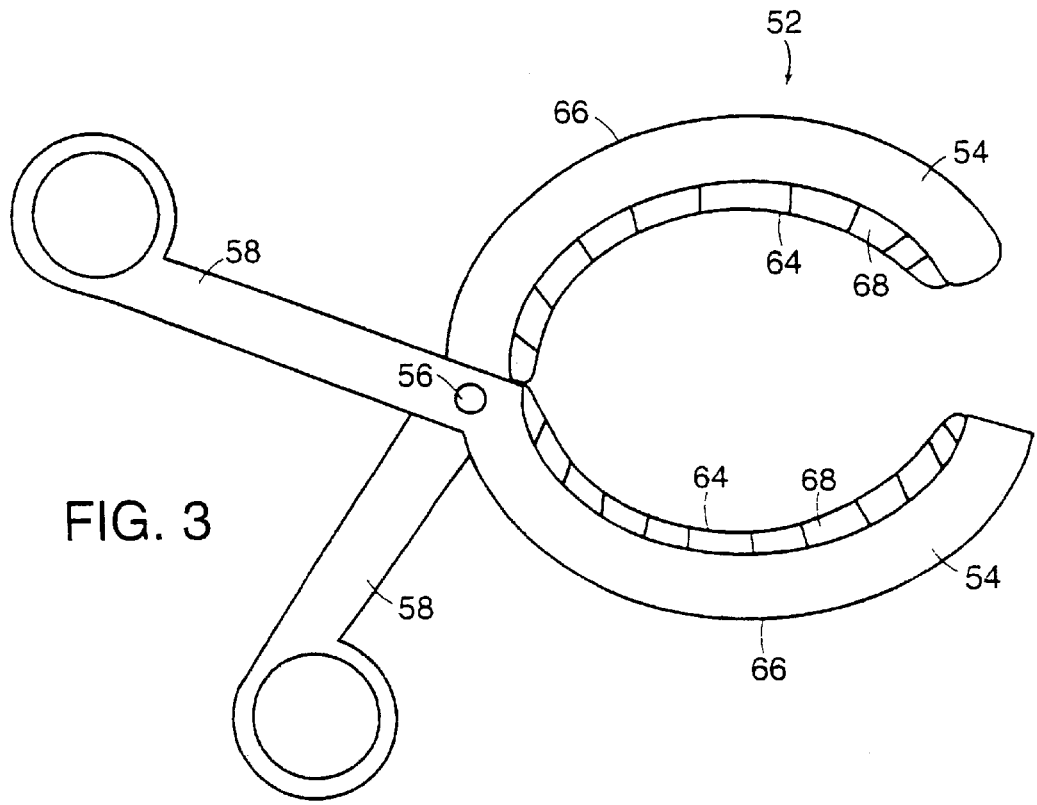
FIG. 3 is a view of an epicardial gripper with two moveable arms and ablators on both arms.
Figure 4:
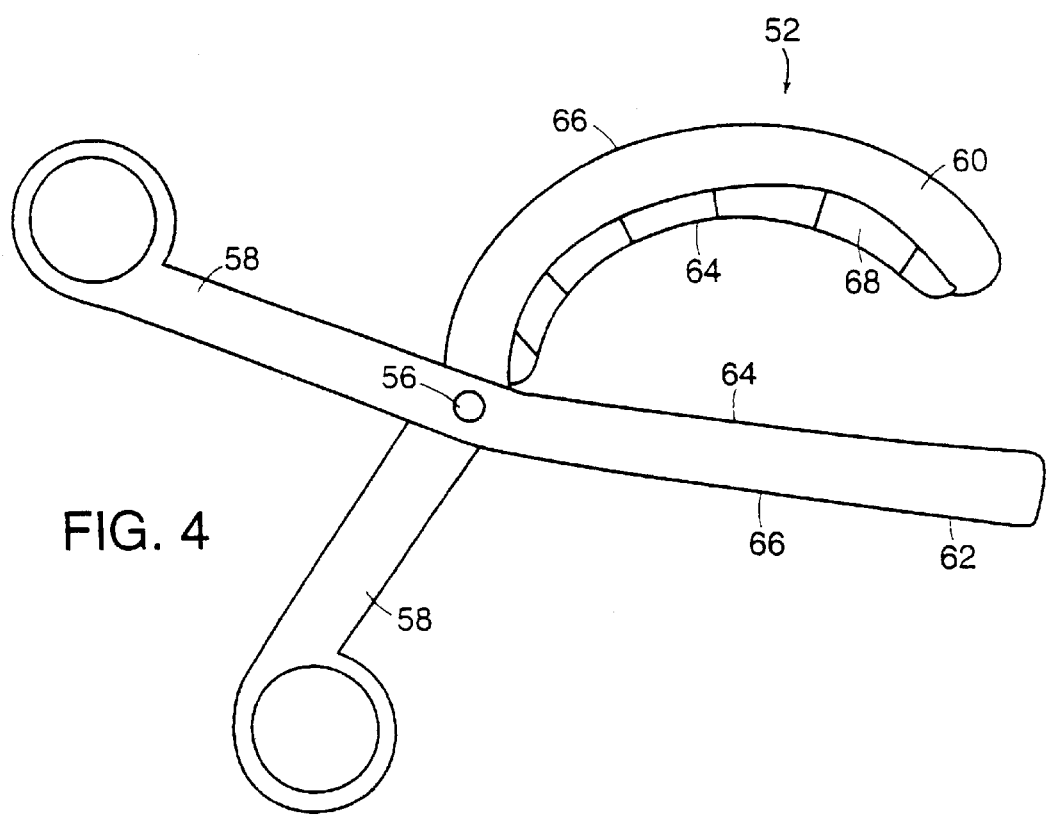
FIG. 4 is a view of an epicardial gripper with one moveable arm with ablators and one fixed arm.
Figure 5A:
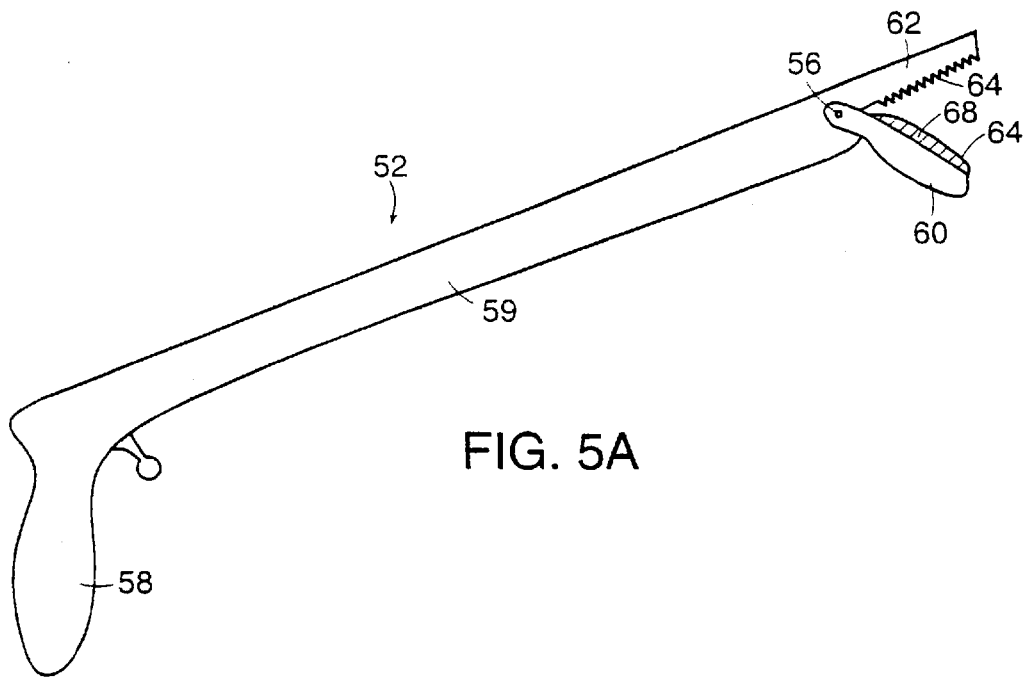
FIG. 5A is a diagrammatic view of another embodiment of the epicardial gripper with one moveable arm and one fixed arm.

In one aspect of the invention as shown in FIG. 3, an epicardial gripper 52 includes at least two arms 54 that pivot around each other at a pivot point 56. The arms 54 of the gripper 52 are each attached to a respective handle 58. In one embodiment as shown in FIG. 3 the arms 54 are moveable relative to each other. In another embodiment shown in FIGS. 4 and 5, the gripper 52 may include two arms wherein one arm is a moveable arm 60 and the remaining arm is a fixed arm 62, relative to the moveable arm. The arms may be disposed at the end of a long barrel 59, for example as illustrated in FIG. 5. In another embodiment, in a multi-arm gripper, one or more arms 62 are fixed while the opposing one or more arms 60 is moveable as shown in FIG. 6. Any number of arms is contemplated, at least one of which is moveable.

Figure 5B:
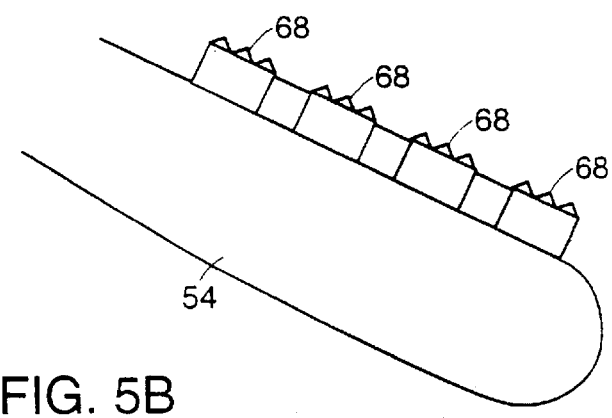
FIG. 5B is an enlarged view of a serrated surface of the ablator.
Figure 6:
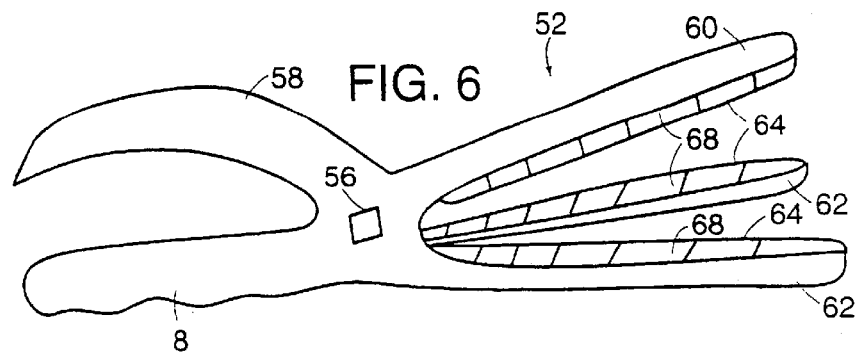
FIG. 6 is a diagrammatic view of another embodiment of the epicardial gripper with one moveable arm and two fixed arms and ablators on the inner surface of all arms.
Figure 7A:
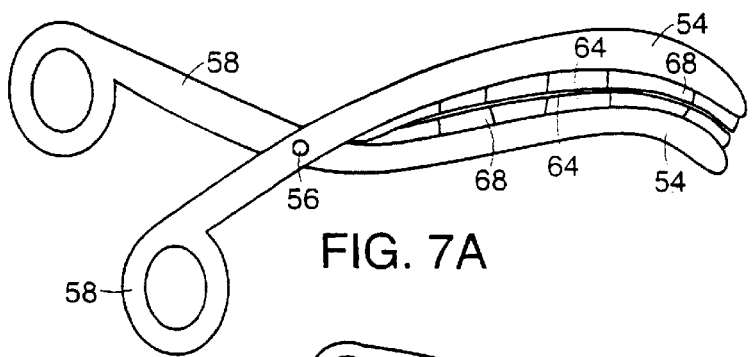
FIG. 7A is a diagrammatic view of another embodiment of an epicardial gripper with two moveable curvilinear arms.
Figure 7B:
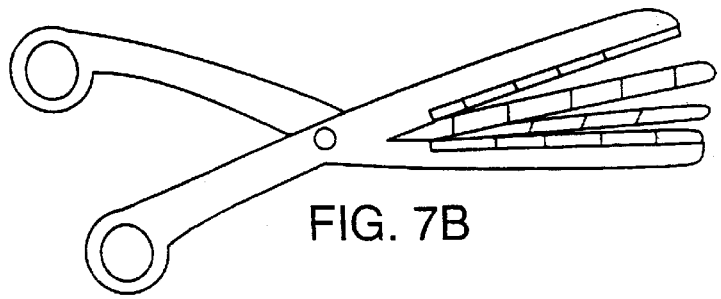
FIG. 7B is a diagrammatic view of another embodiment of an epicardial gripper with two moveable arms in a Y-shaped array.
Figure 7C:
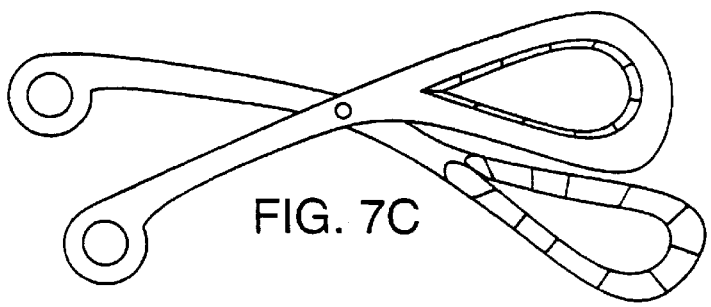
FIG. 7C is a diagrammatic view of another embodiment of an epicardial gripper with two loop-shaped arms.
Figure 7D:
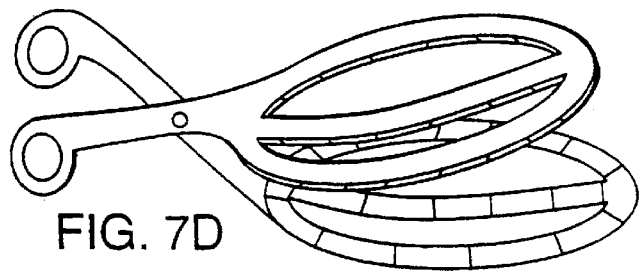
FIG. 7D is a diagrammatic view of another embodiment of an epicardial gripper with two multi-element spokes as arrays.

In one embodiment, as illustrated in FIG. 5B, the ablation surface, non-ablation elements in contact with the heart tissue or both are serrated or irregular in contour to increase friction.

As shown in FIGS. 3–9, the arms 54 of the gripper 52 generally comprise an elongate body pre-formed into a generally curved or curvilinear shape. The shape corresponds to the geometry of the epicardial surface to be ablated.

The arms of the gripper are formed from an electrically non-conductive, inert, material. Suitable materials for the arms include, but are not limited to, Pebax®, polyethylene, or polyester. Other materials, with the above characteristics, which retain their shape at body temperature are also contemplated. The gripper may be formed of shape memory materials, for example, nitinol. The gripper may be enclosed within a sheath dimensioned for insertion through a small orifice. After the gripper is inserted, the sheath is removed and the gripper arms assume a pre-formed shape.

Each of the arms of the gripper 52 have an inner surface 64 and an outer surface 66 defining a cross section. The cross section may be substantially circular, semi-circular, rectangular, V-shaped, D-shaped or the cross-section may have multiple radii as illustrated in FIGS. 10A–J. In one embodiment, ablators 68 may be positioned on the inner surface 64 as shown in FIGS. 3–9. Ablators ablate cardiac tissue. Ablation destroys or removes the function of tissue. In some cases ablation is followed by revascularization of the cardiac tissue. As shown in cross section in FIG. 10, in other embodiments the ablators are disposed on one or more surfaces of one or more arms. In various embodiments, as illustrated in FIGS. 3–9, ablators are positioned on one or more moveable arms, one or more fixed arms, or both.

Ablators may be positioned on the arms in a variety of ways. In one embodiment, the ablator is a single, linear ablator as shown in FIGS. 3–8. In another embodiment, multiple ablators may be arranged on the arms in a patterned array, such as, for example, a linear array as illustrated in FIG. 9. The spacing of the ablators depend on the geometry of the tissue to be ablated. The number of ablators and the dimensions of individual ablators may be determined by tissue geometry, the arm shape, and the requirement for arm flexibility. In one embodiment, each ablator is preferably made of platinum, about 0.2–5 mm thick and about 1–5 mm long. In another embodiment, the platinum is preferably 2 mm thick and preferably about 4 mm long. In yet another embodiment, the ablators comprise detachable, reattachable ablators.

In one embodiment, prior to securing the ablators to the arms, each of the ablators is attached to a low resistance conductor wire threaded through holes in the arm. In one embodiment, the ablating energy in each ablator is individually controllable.

Figure 11A:
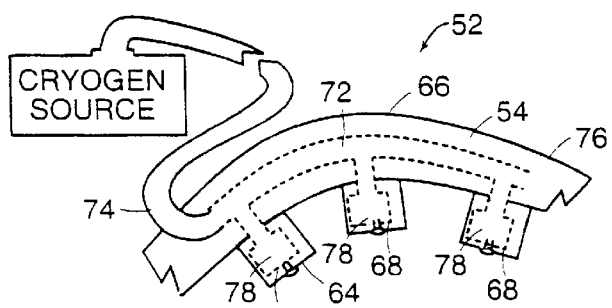
FIG. 11A is a diagrammatic view of multi-element cooling ablators in a portion of the arm of the gripper.
Figure 11B:
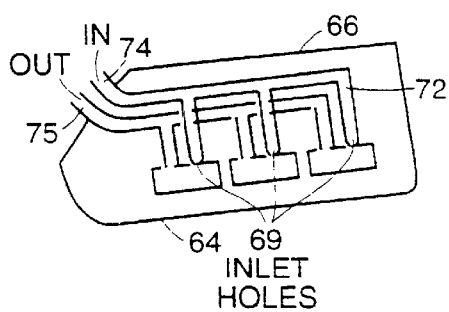
FIG. 11B is a diagrammatic view of another embodiment of the cooling ablators.

In another embodiment of the gripper as shown in FIG. 11A, the ablators 68 are cooling elements as known to one skilled in the art. The arms 54 of the gripper 52 have an interior lumen 72, the proximate end 74 of the lumen 72 in communication with a connection port (not shown) in the handle 58. The lumen 72 communicates with a hollow cavity 78 formed in the ablator 68. In FIG. 11B, inlet holes 69 connect the incoming fluid to a lower pressure object.

Cooling may be accomplished by the delivery of a fluid or gas to the ablators 68 contained within the gripper arms. The cooling fluid may recirculate or exit via small holes in the arms. Cooling is achieved by delivering fluid or gas to the arms via one or more tubes. The gas may exit via one or more tubes. The fluid or gas may come in direct contact with the ablators or be separated from the ablators by a surface.

The cryoablation gripper device may consist of one or more elements consisting of a delivery tube for the entrance of the cryogen. As shown in FIG. 11B, there are one or more small orifices 69 at the ablation surface. At these orifices the cryogen goes from a high to low pressure creating the cooling. These may or may not be a pressure change only or a phase change (FIG. 11B). There may be one or more delivery tubes 74 and one or more tubes 75 that take the fluid or gas back to the proximal end.

Figure 12A:
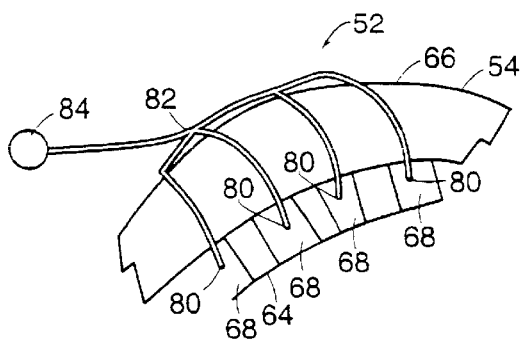
FIG. 12A is a diagrammatic view of laser ablators in a portion of the arm of the gripper.
Figure 12C:
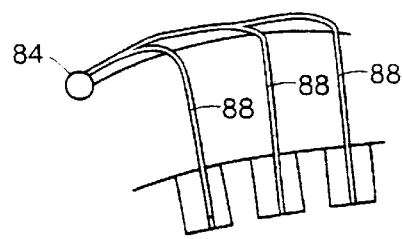
FIG. 12C is another embodiment of laser ablation wherein the ablators are optical fibers connected to a laser source.
Figure 12B:
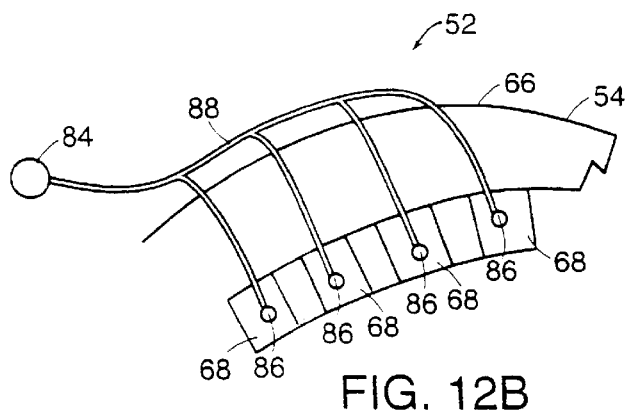
FIG. 12B is another embodiment of laser ablators wherein the ablators are lenses in the arm of the gripper attached by optical fibers to a laser source.

In another embodiment, the ablators are lasers. In one embodiment shown in FIG. 12A, the laser ablators 80 are disposed along the inner surface 64 of an arm 54 in an array, such as a linear array. The lasers 80 are attached to conductor wire 82 leading to an energy source 84. In another embodiment shown in FIG. 12B the laser ablators are lenses 86 attached by fiber optics 88 to a laser source 84. In another embodiment shown in FIG. 12C the laser ablators are optical fibers 88 attached to a laser source 84. In another embodiment (not shown) the ablator is an ultrasound transducer.

The gripper may have one or more suction elements. The suction device consists of a small hole which is along the contact surface of the gripper. This hole is attached to a tube which exits from the gripper. Suction is achieved by creating negative pressure within this tube using an apparatus outside the body. In another embodiment these suction elements consist of suction cups which create suction when contact pressure is applied.

Figure 8:
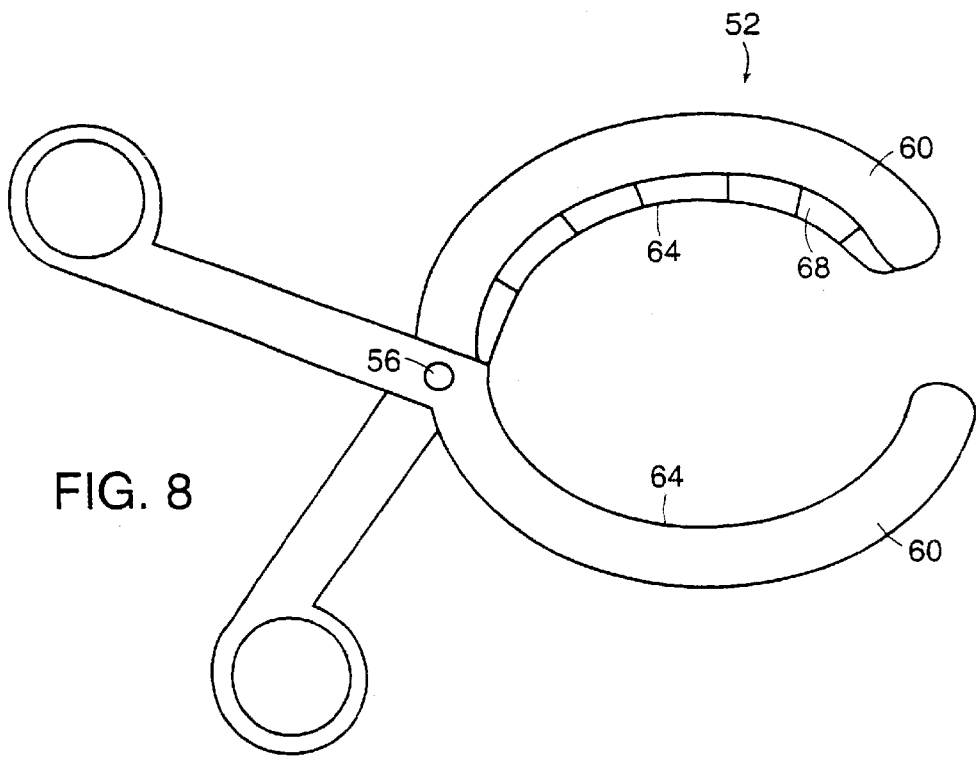
FIG. 8 is a diagrammatic view of another embodiment of an epicardial gripper with two moveable arms and ablators on one of the two moveable arms.
Figure 9:
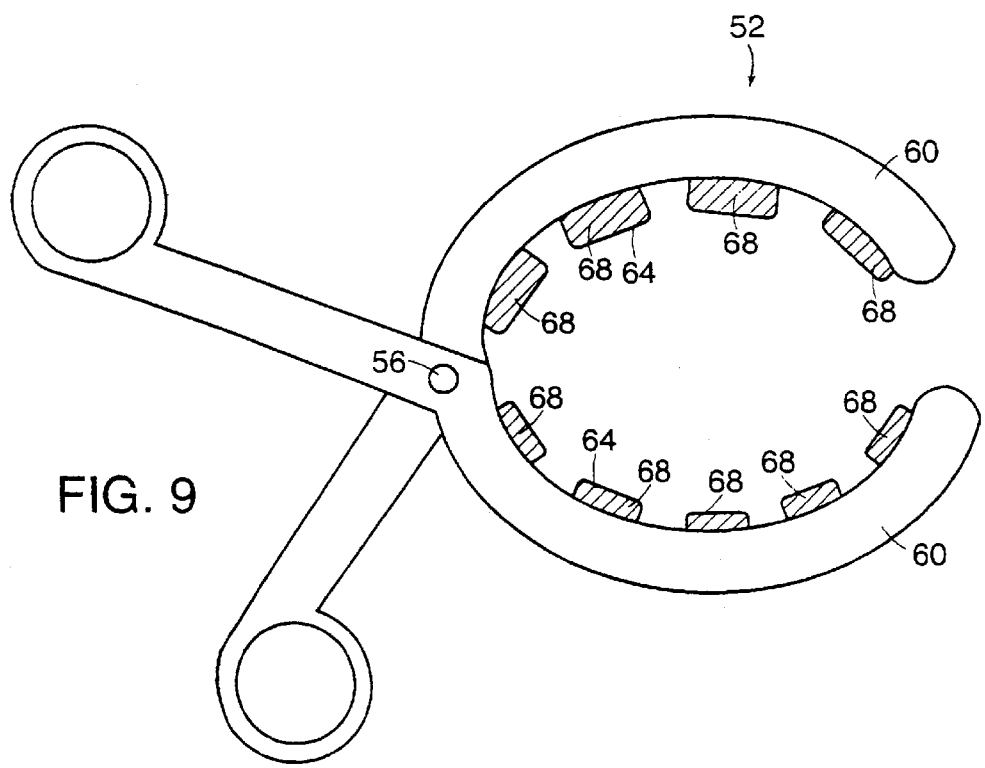
FIG. 9 is a diagrammatic view of another embodiment of an epicardial gripper with multiple ablators disposed on the inner surface of both arms of the gripper.

In a preferred embodiment shown in FIG. 8, the gripper 52 comprises two moveable arms 60 configured to act as a clamp. A linear array of continuous or discontinuous ablation elements or a single continuous linear ablator 68 is located on one arm 60. In clinical use, the arms 60 are disposed about the circumference of the heart on the epicardial surface. The arm with the one or more ablators is aligned such that the ablator is positioned over the tissue to be ablated. The opposing arm without ablators is disposed on the opposite side of the heart to stabilize the gripper on the epicardial surface. In one embodiment, when the alignment of the ablating arms with the myocardial tissue to be ablated is satisfactory as known by a skilled artisan, ablating energy is applied. Sufficient ablating energy is applied to the ablators to ablate cardiac tissue as required.

In an alternate embodiment (not shown), the gripper comprises an ablating arm and a non-ablating arm. The ablating arm is inserted through an incision made by a surgeon through the wall of the heart. The ablating arm is aligned with the region of the endocardial surface to be ablated and the non-ablating arm is disposed on the epicardial surface to stabilize the gripper. When the ablating arm is aligned by the surgeon with the endocardial surface to be ablated, sufficient ablating energy is supplied to the ablators to ablate the cardiac tissue as desired.

The gripper device is designed to ablate cardiac tissues. The gripper is able to maintain stable contact with the epicardial surface by partially or completely encompassing a circumference of a part of the heart. The ablation may be performed on any portion of the epicardial surface with which the gripper has contact. The ability of the gripper to partially or completely encompass a circumference of a part of the heart creates stability and allows for contact by conforming to the epicardial surface of the heart. Ablation may be performed in a linear or curvilinear arrangement.

Figure 13:
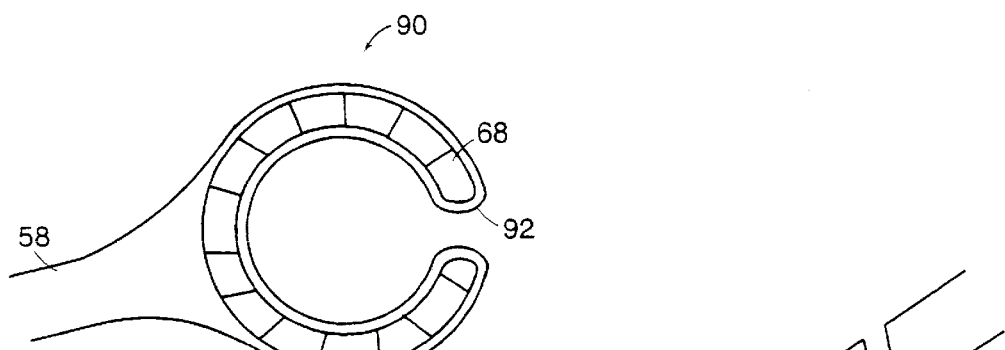
FIG. 13 is a diagrammatic view of the adjustable, flexible probe substantially forming a loop of the electrode system.
Figure 14A:
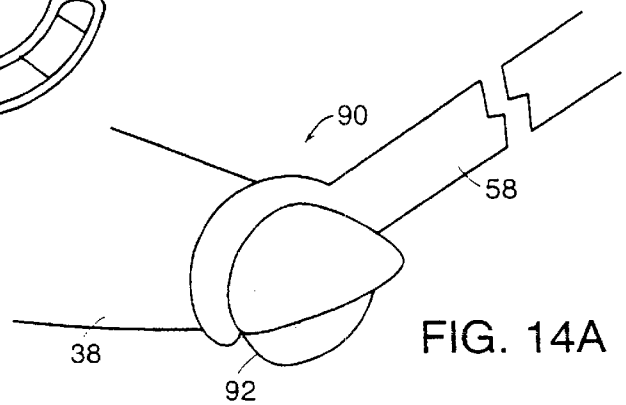
FIG. 14A is a diagrammatic view of the adjustable, flexible probe substantially encompassing an auricle of the heart.
Figure 14B:
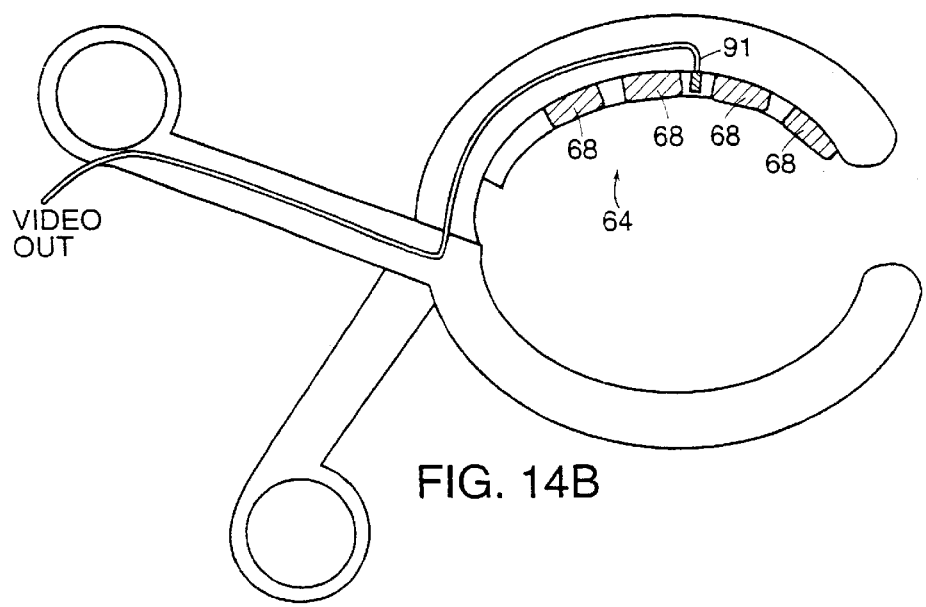
FIG. 14B shows a camera permitting visualization of the cardiac surface.

In another embodiment, the invention is an electrode system for epicardial ablation of cardiac tissue. As illustrated in FIG. 13 the electrode system 90 comprises a handle 58. Attached to one end of the handle 58 is a probe 92 comprised of an adjustable, flexible substrate forming a substantially closed loop. The loop is sized to substantially encompass a structure of the heart such as an auricle 38 as shown in FIG. 14. The probe 92 has at least one contact surface. At least one ablator 68 is positioned on at least one contact surface.

In one embodiment of the gripper, an ultrasound probe is placed on the inner surface of the gripper in order to assess contact with the heart surface and depth of ablation lesion.

In one embodiment of the gripper, an optical fiber with or without a lens is placed on the inner surface of the gripper in order to assess positioning and contact. The optical fiber is attached to a camera outside of the body. In one embodiment illustrated in FIG. 14B a miniature camera 91 is placed on the inner or other surface of the gripper in order to assess positioning and contact.

Figure 10A:
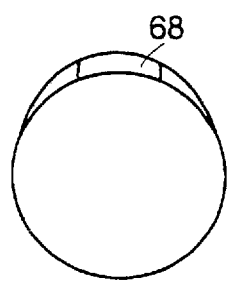
FIGS. 10A–J is a cross sectional diagrammatic view of the various arrays of ablators on the surface of the arm of the epicardial gripper or the surface of the probe of the electrode system.
Figure 10B:
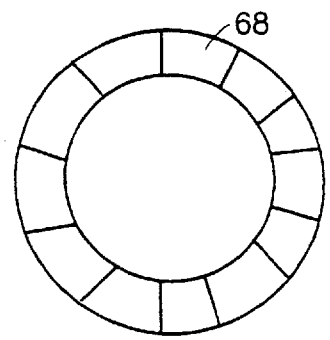
Figure 10C:
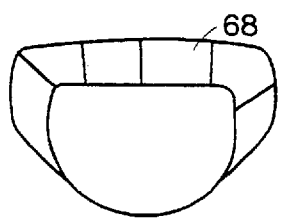
Figure 10D:
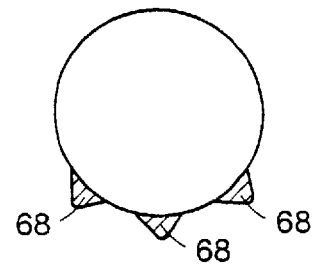
Figure 10E:
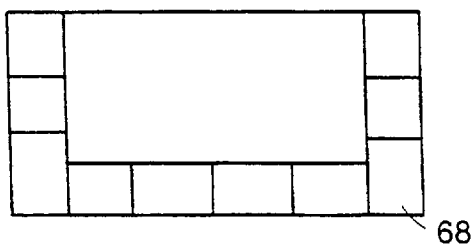
Figure 10F:
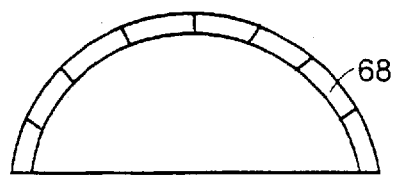
Figure 10G:
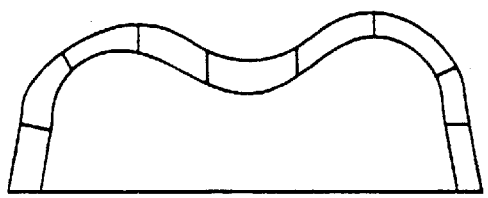
Figure 10H:
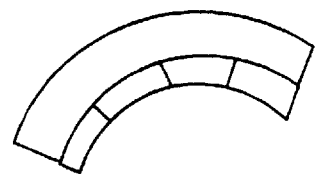
Figure 10I:
Figure 10J:
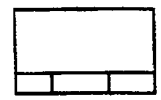

The probe 92 of the electrode system 90 is formed from a non-conductive, flexible, adjustable material. Suitable materials for the probe include but are not limited to Pebax, polyethylene, polyester, polyurethane, silicone and Teflon. The probe may be formed of shape memory materials, for example, nitinol. The probe may be enclosed within a sheath dimensioned for insertion through a small orifice. After the probe is inserted, the sheath is removed and the probe assumes a pre-formed shape. As illustrated in FIGS. 10A–J, the probe comprises a cross section defined by the probe surfaces, at least one surface being a contact surface. As illustrated in FIG. 10C or 10F, in one embodiment, the cross section of the probe may be substantially D-shaped. In other embodiments shown in FIGS. 10A–J, the cross section of the probe may be circular, semi-circular, rectangular, V-shaped, D-shaped or the cross section may have multiple radii.

Figure 15:
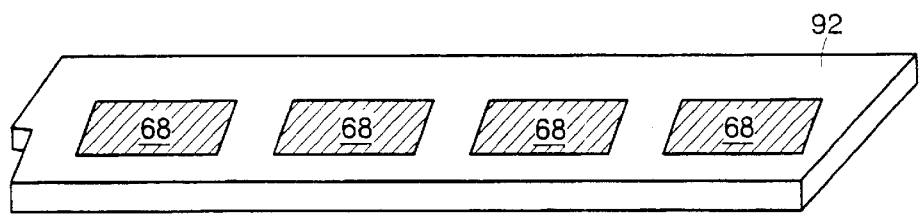
FIG. 15 is a diagrammatic view of the surface of the probe with the ablators arranged in a linear array.

The electrode system 90 includes one ablator or a plurality of ablators. The one or more ablators 68 positioned on the probe 92 is arranged in any array, such as a linear array. The spacing between ablators 68 depends on the geometry of the cardiac tissue to be ablated. The number of ablators, position of the ablators, and dimension of the ablators depend on the geometry of the cardiac tissue to be ablated, the surface of the probe on which the ablators are placed and the requirements for probe flexibility. In one embodiment, as illustrated in FIG. 15, multiple ablators 68 are arranged in a linear array along one contact surface of the probe 92, the probe 92 having a substantially rectangular cross section. In other embodiments as illustrated in cross section of FIG. 10A, a single long ablator or multiple continuous or discontinuous ablator elements may be longitudinally disposed on one semicircle of a probe the probe having a substantially circular cross section. In still other embodiments as illustrated in FIGS. 10C–J, the ablators may be positioned around the circumference of the probe, around three sides of a substantially D-shaped probe, as multiple points, or around one to three sides of a substantially rectangular probe.

In one embodiment, each ablator is attached to a low resistance conductor wire threaded through holes in the probe. In another embodiment the ablating energy of each ablator is individually controllable.

Each ablator is connected to a low resistance conductor wire. Energy may be delivered to one or more of these ablators at one time (simultaneous energy delivery) or energy may be delivered sequentially. Energy delivery may be delivered in a repetitive and sequential manner e.g. x ms for electrode 1, y ms for electrode 2, z ms for electrode 3, and so on, followed again by x ms for electrode 1, y ms for electrode 2, z ms for electrode 3 and so on where x, y and z are real numbers. The time between energy delivery between electrodes n and n+1 may be 0 ms or a value greater than 0 ms.

Activation of the electrode energy delivery may be achieved by a control box which is manually activated or activated by an electronic control. A microprocessor may be used to activate energy delivery.

One or more optical fibers may be organized in a linear (one or more rows) or curvilinear array or other geometric pattern such as an oval along the inner surface of the gripper. These may be individually or simultaneously activated with laser energy.

Figure 16A:
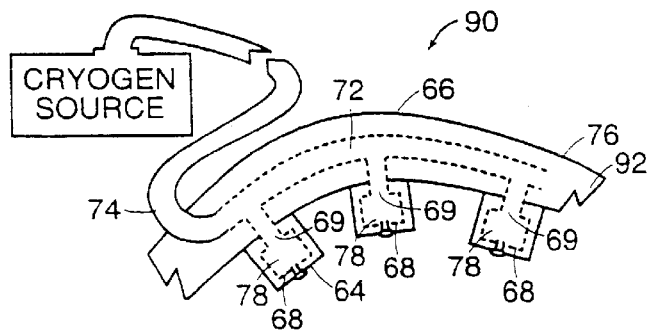
FIGS. 16A–B is a diagrammatic view of cooling ablators in a portion of the probe of the electrode system.
Figure 16B:
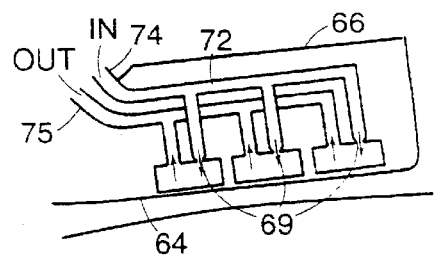

In one embodiment of the electrode system 90 as shown in FIG. 16A, the ablators 68 are cooling elements. The probe 92 of the electrode system 90 includes an interior lumen 72, the proximate end 24 of the lumen 72 in communication with a connection port in the handle (not shown) as is known to one skilled in the art. The lumen 72 communicates with a hollow cavity 78 formed in the ablator. Cooling may be accomplished by the delivery of a fluid or gas to the ablators contained within the probe. The cooling fluid may recirculate (FIG. 16A) or exit via small holes in the device. Cooling is achieved by delivering fluid or gas to the arms via one or more tubes 74. It may exit via one or more tubes 75 as shown in FIG. 16B. The fluid or gas may come in direct contact with the ablators or be separated from the ablators by a surface. This surface may be thermally conductive or non conductive. The cryoablation device may consist of one or more elements consisting of a delivery tube for the entrance of the cryogen. There are one or more small orifices 69. At these orifices 69 the cryogen passes from a high to low pressure creating the cooling. In the embodiment shown in FIG. 16B there may be a pressure change only or a phase change. In the embodiment shown in FIG. 16A there is no pressure change.

Figure 17A:
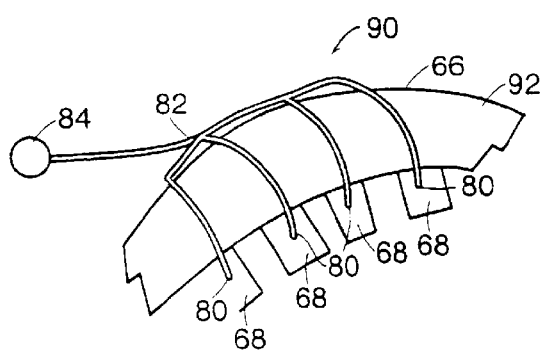
FIG. 17A is a diagrammatic view of laser ablators in a portion of the probe of the electrode system.
Figure 17C:
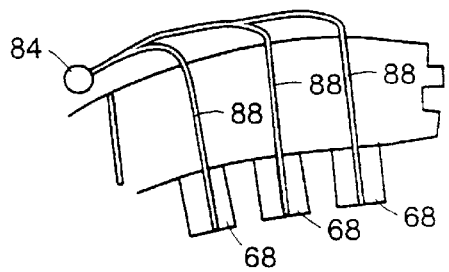
FIG. 17C is another embodiment of laser ablation wherein the ablators are optical fibers connected to a laser source.
Figure 17B:
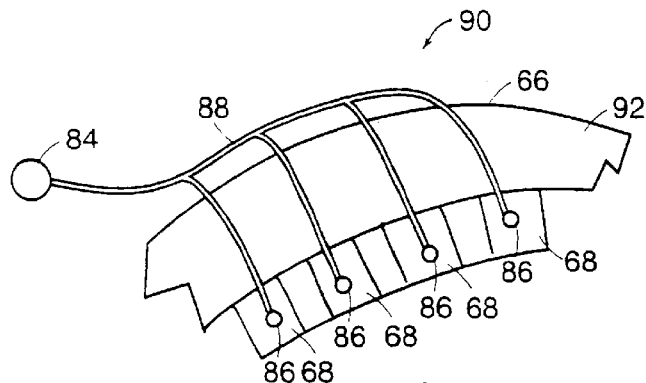
FIG. 17B is another embodiment of laser ablators wherein the ablators are lenses in the probe of the electrode system attached by fiber optics to a laser source.

In another embodiment, the ablators 68 are lasers. In one embodiment shown in FIG. 17A, the laser ablators 80 are disposed along the inner surface of the probe in an array, such as a linear array. The lasers 80 are attached to conductor wire 82 leading to an energy source 84. In another embodiment illustrated in FIG. 17B, the laser ablators 80 are lenses 86 attached by fiber optics 88 to a laser source. In another embodiment shown in FIG. 17C the laser ablators are optical fibers attached to a laser source.

In one embodiment (not shown) the ablators are ultrasound transducers. The ablators in another embodiment are made of platinum. In one embodiment, the platinum is about 0.2–5 mm thick and about 1–5 mm long. In another embodiment, the platinum is about 2 mm thick and about 4 mm long.

The ablators of the electrode system provide ablating energy from any energy source known in the art including, but not limited to, radio frequency energy, laser energy, direct current, or ultrasound. In another embodiment the ablators may use low temperatures, achieved by cryogens, for example, to ablate cardiac tissue.

Figure 20:
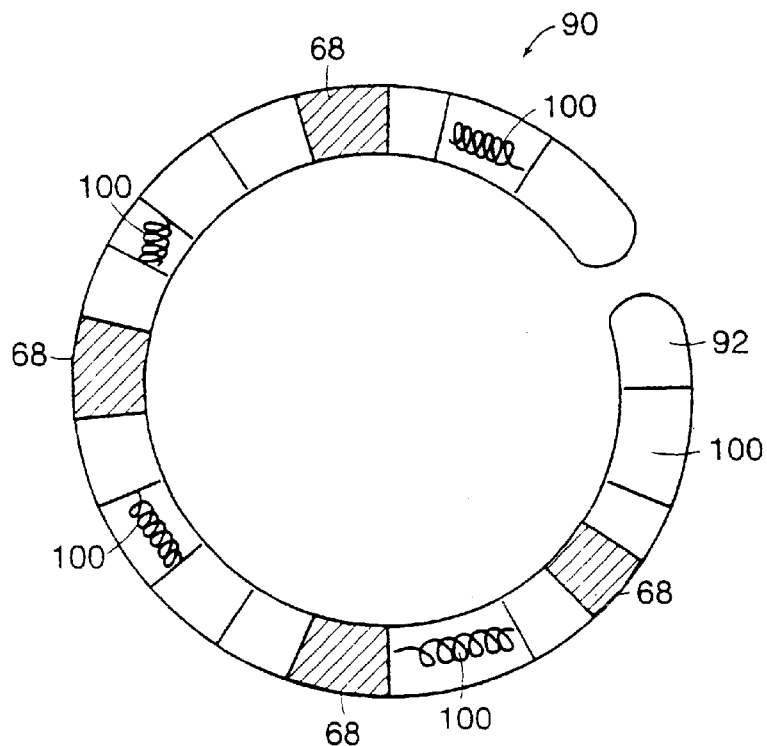
FIG. 20 is a diagrammatic view of the spring-adjustable flexible probe of the electrode system.
Figure 19:
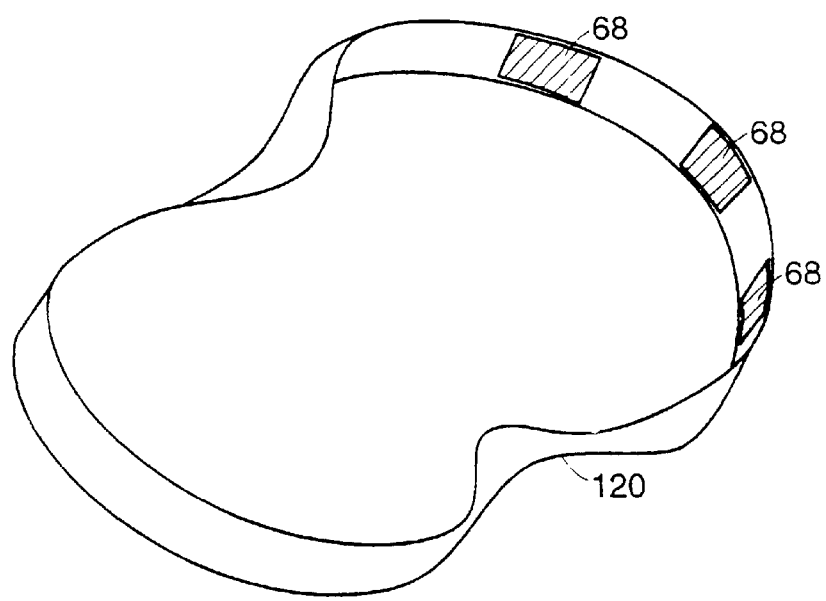
FIG. 19 is a diagrammatic view of the adjustable, flexible probe made of elastomeric materials.

In one embodiment of the electrode system show in FIGS. 18A and B, the loop of the probe may be adjusted by a pull-string 94 disposed in a channel 102 within the probe 92. Moving the end 98 of the pull-string 94 in the direction of the arrow 96 shown in FIG. 18A, substantially closes the probe loop as shown in FIG. 18B. In another embodiment, as illustrated in FIG. 18C, the pull-string 94 is attached to the end 120 of probe 92, and passes through a collar 126. Moving the end of the string 94 in the direction of the arrow 96, adjusts the size of the probe loop. In another embodiment shown in FIG. 19 the probe is comprised of an elastomeric material for adjusting the size and dimensions of the loop. In yet another embodiment shown in FIG. 20 of the electrode system 90, the size and dimensions of the loop is adjusted by springs 100 or elastic material interposed between ablators 68 on the probe 92 surface.

In another embodiment, attachment devices may be in communication with the probe, for example, a gripping device, such as a suction device. The probe may have one or more suction elements. The suction device consists of a small hole which is located along the contact surface of the probe. This hole is attached to a tube which exits from the probe. Suction is achieved by creating negative pressure within this tube using an apparatus outside the body. In another embodiment these suction elements consist of suction cups which create suction when contact pressure is applied.

In still another embodiment, the electrode system comprises a glove having at least one ablator on a probe, the probe being in communication with the finger on the glove. In another embodiment the probe and ablators may be in communication with multiple fingers of the glove. The ablators are placed on one or more surfaces of the glove. The ablators may be arranged in a linear or curvilinear array. These ablators may be on the inner or outer surface of the curvature of the glove. For example, electrical ablator conductor wires are attached to the ablators and exit from the glove to the energy source. In another embodiment using lasers, optical fibers are positioned on the surface of the glove and exit from the glove to the laser source. In another embodiment using cryoablation, the individual or single cryoablation probe or elements are attached to surface of the glove and exit from the glove to the source of the cryogen.

In one embodiment, the electrode system is sized and shaped for insertion through an endoscope or thoracoscope.

The gripper and the flexible electrode are used to create myocardial ablative lesions from the epicardial and/or endocardial surface of the heart. These devices are placed in contact with the epicardial surface of the heart and energy is delivered. Contact is maintained because of the shape of the device and the ability of the device to conform to and be stabilized on the epicardial surface of the heart via friction, or suction.

Figure 21:
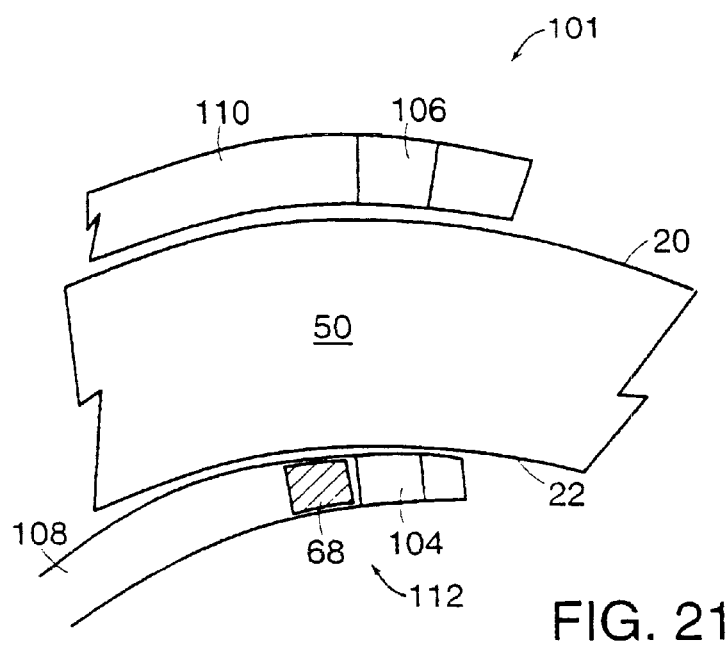
FIG. 21 is a cross-sectional view of the myocardium and endocardial ablator detection system.

Another aspect of the invention comprises a system for detection of ablators localized on endocardial ablating catheters and related devices. The ablator detection system 101, illustrated in FIG. 21, comprises a detector 106 at the epicardial surface 20, at least one indicator 104, at least one ablator 68, an endocardial catheter 108 adjacent the endocardial surface 22 and an epicardial probe 110. In another embodiment the detector 106 is present adjacent to the endocardial surface 22 and the indicator 104 is on the epicardial probe 110.

Referring again to FIG. 21, a system 101 for detection of endocardial ablators localized on endocardial ablating catheters 108 includes an indicator 104 localized adjacent an ablator 68 positioned on the endocardial catheter 108 and a detector 106. The indicator 104 transmits signals indicating the position of the ablator 68 on the ablating catheter 108 inserted into a heart chamber 112. A detector 106 positioned on an epicardial probe 110 detects the position of the endocardial indicator 104 adjacent the ablator 68 on the endocardial catheter 108. When the ablator 68 is appropriately aligned with the cardiac tissue to be ablated as detected by the epicardial detector, ablating energy is applied to ablate myocardial tissue through the endocardium 22. In another embodiment the detector 106 is on the endocardial catheter 108 and the indicator 104 is on the epicardial probe 110.

In one embodiment, the indicator 104 and/or the detector 106 is a magnet. A magnet may be present within or attached to the endocardial catheter and the epicardial probe. In another embodiment either the endocardial catheter or epicardial probe have a magnet and the other element has a metal attracted by a magnet. The magnet may be a natural magnet or an electromagnet. The polarities of the magnets are selected so that the endocardial and epicardial magnets metal or elements attract. The endocardial catheter or epicardial probe may be positioned so that they are precisely aligned by using one or more magnets with each element.

In another embodiment, the indicator is a light source, for example, laser light. In one embodiment, there is no detector on the epicardial surface. The light is seen by the operator visually. In another embodiment there is an optical fiber on the epicardial probe to detect the light from the indicator. The optical fiber may be connected to a video camera. In another embodiment a miniature video camera is placed on the epicardial probe. The light source on the catheter may be circumferential or only on one surface of the catheter. In one embodiment, the light source is on only one surface and the electrode or energy elements are only on the same surface to permit alignment. The detector 106 is positioned on an epicardial probe 110. The probe 110 is sized to fit a hand, formed from a flexible, inert substrate and dimensioned to abut an epicardial surface. In one embodiment, probes may be cylindrical and held like a pen with the interfacing region positioned at the end of the probe. In another embodiment, the probe may be rectangular or cylindrical with the interfacing region positioned on the side of the probe. In one embodiment, the detector is a magnetic field detector.

Alternatively, in another embodiment the detector is a light detector. In still another embodiment the detector is an ultrasound device or an echocardiograph. In one embodiment the ultrasound is used to detect contact with cardiac tissue and depth of lesion ablation.

Figure 22:
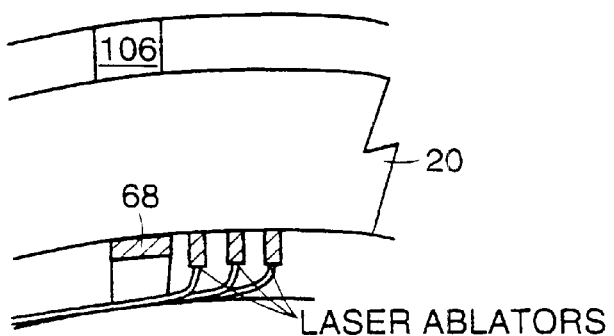
FIG. 22 is a cross-sectional view of the myocardium and a endocardial laser ablator detection system.

In one embodiment ablators are present only on the endocardial catheter or the epicardial probe. The endocardial catheter or epicardial probe are used for positioning and orientation. In one embodiment the endocardial catheter is oriented so that ablation, for example laser ablation, is directed towards the epicardial surface (FIG. 22). In one embodiment the indicator is only on one surface, the surface of the ablation elements.

The endocardial catheter is any endocardial ablating catheter known in the art.

In a clinical application of the ablator detection system, the endocardial ablating catheter is passed through a patient's artery or vein into the heart to the site of arrhythmogenic tissue. Simultaneously, the epicardial detector probe is placed by the surgeon on the epicardial surface of the heart. The indicator positioned adjacent to the ablator on the endocardial catheter transmits signals across the myocardium to the epicardial surface. The signals transmitted by the indicator are detected by the detector on the epicardial probe thereby localizing the position of the endocardial ablator relative to the epicardial surface. The position of the endocardial ablator is adjusted in accordance with its relative position on the epicardial surface and the therapeutic objectives of cardiac ablation. When the endocardial ablator is determined to be appropriately positioned, ablating energy is applied to cause trans-myocardial ablation.

Figure 23:
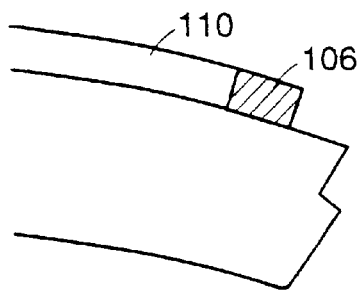
FIG. 23 is a cross-sectional view of the myocardium and an epicardial ultrasound imaging probe.

An epicardial ultrasound imaging probe of dimensions suitable to be inserted in a thoracoscope is used to visualize the anatomy of the heart tissue from the epicardial surface to provide ablation (FIG. 23).

What is claimed is:

1. A method of ablating cardiac tissue from an epicardial location, comprising the steps of:
   providing an ablating device having a plurality of ablating elements, the plurality of ablating elements being coupled to a substrate, the substrate forming a loop with the ablating elements positioned on a radially inner surface of the loop, wherein the ablating elements direct energy inward and not outward relative to the loop to prevent damaging tissue outside the loop;
   positioning the ablating device at an epicardial surface so that the loop is positioned around a cardiac structure; and
   ablating tissue with the ablating elements thereby ablating tissue around the cardiac structure to treat a cardiac arrhythmia.

2. The method of claim 1, wherein:
   the providing step is carried out with the ablating elements directing energy radially inward relative to the loop.

3. The method of claim 1, wherein:
   the providing step is carried out with the loop being a closed loop.

4. The method of claim 1, wherein:
   the positioning step is carried out with the loop being self-retaining around the cardiac structure.

5. The method of claim 1, wherein:
   the providing step is carried out with the device having a band-like shape.

6. The method of claim 1, wherein:
   the providing step is carried out with the loop generally lying in a plane with the ablating elements directing energy radially inward, the device being flexible to permit bending between the ablating elements while still substantially maintaining the loop on the plane.

7. The method of claim 1, wherein:
   the providing step is carried out with the plurality of ablating elements being spaced apart.

8. The method of claim 1, wherein:
   the ablating step is carried out by turning at least some of the ablating elements on and off.

9. The method of claim 8, wherein:
   the ablating step is carried out with the ablating elements being turned on and off sequentially.

10. The method of claim 1, wherein:
    the ablating step is carried out by turning the ablating elements on and off in a specified pattern.

11. The method of claim 1, further comprising the step of:
    using ultrasound to assess whether the contact surface is in contact with the epicardial surface.

12. The method of claim 1, further comprising the step of:
    using ultrasound to determine the depth of ablation.

13. The method of claim 1, wherein:
    the ablating step is carried out to treat tachycardia.

14. The method of claim 1, further comprising the step of:
    cooling the ablating elements.

15. The method of claim 1, wherein:
    the providing step is carried out with the ablating elements being an element selected from the group consisting of RF, ultrasound, laser, and cryogenic elements.

16. The method of claim 1, wherein:
    the providing step is carried out with a contact surface of the ablating element being curved.

* * * * *